United States Patent
Schwartz et al.

(12)

(10) Patent No.: US 6,576,252 B2
(45) Date of Patent: Jun. 10, 2003

(54) ANTI-STRESS COMPOSITION INTENDED FOR INCORPORATION MAINLY IN NUTRITIONAL VEHICLES

(75) Inventors: Robert Schwartz, Paris (FR); Jean-Christophe Anton, Strasbourg (FR); Sylvie Chantereau, La Wantzenau (FR)

(73) Assignee: Laboratoires Robert Schwartz, Illkirch Graffenstaden (FR)

( * ) Notice: Subject to any disclaimer, the term of this patent is extended or adjusted under 35 U.S.C. 154(b) by 0 days.

(21) Appl. No.: 09/853,429

(22) Filed: May 10, 2001

(65) Prior Publication Data

US 2003/0077313 A1 Apr. 24, 2003

(30) Foreign Application Priority Data

Oct. 17, 2000 (FR) .............................. 00 13298

(51) Int. Cl.⁷ .................... A61K 35/78; A61K 47/44
(52) U.S. Cl. ............... 424/439; 424/535; 424/776; 424/725; 514/419
(58) Field of Search ................ 424/535, 725, 424/728, 750, 198.1, 94.1, 439, 776, 283.1; 514/419

(56) References Cited

U.S. PATENT DOCUMENTS

| 4,638,013 A | * | 1/1987 | Moja et al. |
| 5,308,832 A | * | 5/1994 | Garleb et al. |
| 6,025,510 A | * | 2/2000 | Wimmer et al. |
| 6,077,867 A | * | 6/2000 | Pageat |
| 6,080,410 A | * | 6/2000 | Bewicke |
| 6,121,234 A | * | 9/2000 | Benet et al. |

FOREIGN PATENT DOCUMENTS

| EP | 1992-302250 | * | 7/1992 |
| EP | 2000-255057 | * | 2/1999 |
| JP | 61047417 A | * | 3/1986 |

OTHER PUBLICATIONS http://www.graylab.ac.uk/omd/index.html, 1997.*

* cited by examiner

Primary Examiner—Leon B. Lankford, Jr.
Assistant Examiner—Ruth A. Davis
(74) Attorney, Agent, or Firm—Abelman, Frayne & Schwab

(57) ABSTRACT

A composition to provide a calming stress hormone regulating and immune stimulation effect, which includes a combination of linoleic and linolenic acids, within certain ratios; at least one flavenoid; and at least one component having calming properties.

18 Claims, No Drawings

ANTI-STRESS COMPOSITION INTENDED FOR INCORPORATION MAINLY IN NUTRITIONAL VEHICLES

The present invention relates to a composition for obtaining a triple calming, stress hormone regulating and immune stimulation effect.

It is now scientifically established that stress develops through the following three phases:

in a first stage, the body reacts to an external aggression situation with an alarm reaction which is revealed through several physical signs, including mainly an accelerated cardiac rhythm, short and rapid respiration, general increase in muscular tension and dryness of the throat. The purpose of this reaction is to improve oxygenation of the tissues and to distribute the blood differently in the organism, in particular towards its periphery. These mechanisms, set in action by the body, in principle confer on the individual physical dispositions allowing him to fight against external aggression;

in a second stage, resistance can be organised: the organism is in principle provided to adapt to the aggression, as it has available all the nutrients (oxygen, glucose, adenosine triphosphate release) permitting it to resist the experienced situation over a short or medium term period. It does in fact implement what it is convenient to call a "survival strategy". However, the mechanisms contributed by the body may be adequate or inadequate compared with the optimum response which can be made. During this phase, intellectual performance diminished, and a tendency is observed in the patient to become depressed and even to abuse alcohol or other drugs;

then comes the exhaustion stage: the physical signs are very high muscle tension, with frequent headaches and migraines and intestinal troubles (spasms and pains). In certain cases, the appearance of ulcers is noted and, generally, there is an effect of strengthening of subjacent pathologies. At this stage, the depressive syndrome is complete.

In the course of these three phases, the nervous system comes into play with secretion of different hormones. The most well-known are adrenaline (secreted on the initial alarm reaction), cortisol and corticosterone. Other monoamines are also synthesised and released. The increase in these hormones following a stress situation gives the organism the means for its defence by storing energy, mobilising reserves and desensitising it to certain types of aggressions such as pain. In the medium and long term, however, the effects of these hormones are detrimental, even disastrous. They cause tiring of the organism, make it vulnerable to infections (reduction of immune defences) and damage the neurones (memory loss). These effects finally have an impact inter alia on the cardio-vascular system, ageing of the organism and certain conditions of appearance of cancer.

Thus, the elevation of the cortisol level in the plasma can be related to pathologies such as agitation and mood modification and deterioration of the memory mechanisms causing cognitive deficiencies. Recent experiments confirm that high concentrations of cortisol cause cerebral damage at the neuronal level. It is also known that stress is thought to be at the origin of modulation of several aspects or cellular immune response. This is thought to be the result of problems in the transfer of signals between the central nervous system and the immune system which occur partly through the hormone system.

Lastly, anxiety caused by stress has consequences in particular for sleep, lack of which is involved in tiring the organism.

Generally, taking into account the present knowledge of stress mechanisms, any consideration relating to protection of the organism against the damaging effects due to stress can therefore be oriented in the following directions:

protecting the cells and organs against excess cortisol (neural protection);

reinforcing the immune defences (immune stimulation);

taking action on anxiety by means of a calming effect.

This is the main aim of the invention, which recognises the importance of this triple mechanism and to this end proposes a composition having at the same time a calming, stress hormone regulating and immune stimulation effect. The composition is characterised by the fact that it includes:

at least one component including in particular a combination of linoleic and linolenic acids in a ratio permitting reduction of the production of stress hormones;

at least one component taken from the flavonoid group;

at least one component having calming properties.

Recent research has revealed advantageous properties of linoleic and alpha-linolenic acids relating to the regulation of cortisol counts. According to these studies, it does not seem that the quantity of linoleic and/or linolenic acid itself has a beneficial influence, but rather the ratio between these two acids. This beneficial effect would be the result of an improved bio-availability in the brain of the active principles, the said ratio being capable of crossing the haemato-encephalic barrier and the increasing membrane fluidity (essential for the functioning of the nervous system).

Preferably, the linoleic and linolenic acids are combined in a proportion by weight of 58% and 13% respectively.

Preferably again, the component including the combination of linolenic and linoleic acids is nut oil. This natural, easily available product has the advantage of not requiring preparatory work or complex synthesis.

It has long been known, moreover, that certain flavonoids (for example, ginseng including ginsenosides and other saponines) improve physical endurance and mental capacities both in man and animals. For example, the tonic properties of ginseng have been studied with regard to different parameters such as appetite, sleep, absence of mood change, work efficiency, etc. Ginseng also regulates the concentrations of corticosteroids, studies in animals having shown that ginseng decreased the concentrations of cortisol in the blood. Other studies have revealed its immuno-stimulant action. Thus, these flavonoids in themselves have both a calming, stress hormone regulating and immuno-stimulant effect.

Lastly, certain plant extracts, in known manner, have a particularly advantageous calming and sedative effect. Such is true of extracts of hops (Humulus lupulus). Studies have shown that these extracts have an antispasmodic activity on different preparations of isolated smooth muscles and sedative properties leading to an improved aptitude to confront stress and edginess.

The composition of the invention can also contain tryptophane, as component having sedative properties. The use of tryptophane results from the observation of the effects of 5-hydroxytryptophane (synthesised in the organism from tryptophane) which is one of the close precursors of serotonin. This, present at the level of the brain, the blood platelets and the gastro-intestinal apparatus, permits regulation of mood, behaviour and the sleep cycle. Thus tryptophane and its metabolite are theoretically capable of having similar therapeutic effects, without the side effects. It is known in particular that people suffering from chronic insomnia respond well to tryptophane when it is administered in a low dose in repeated manner.

Preferably, the tryptophane used in the invention is contributed by a fraction of milk proteins and represents a percentage by weight of the order of 3% of this fraction.

The different elements participating in the composition of the invention thus lead to the triple result required, the different constituents acting in combination and mutually strengthening their effects.

In accordance with one possibility, the composition of the invention also comprises extract of althaea (marshmallow), containing inter alia a substance having an immuno-stimulant effect (arabinogalactane).

The composition of the invention must of course be administered in a dose and at a frequency calculated for the patient to be able to feel the beneficial effects by obtaining the above-mentioned triple effect. Thus, for daily use, the composition of the invention comprises the following proportions by weight:

600 to 4000 mg of nut oil;
  extract of ginseng such that the quantity of ginsenosides is between 1 and 30 mg;
  100 to 400 mg of hop extract DE;
  40 to 1000 mg fraction of milk proteins.

In accordance with a preferred dosage, the composition consists of:

720 mg nut oil;
  13 mg extract of ginseng such that the quantity of ginsenosides is equal to 1.6 mg;
  150 mg hop extract DE;
  40 mg fraction of milk proteins.

In addition, in accordance with one possibility, extract of althaea is present to the extent of 10 mg.

In order to facilitate absorption of the said composition by the body, different packagings and vehicles are proposed:

capsules;
  phials;
  microspheres;
  confectionery products (e.g. chocolates);
  preparations for cold or hot drinks (e.g. tisanes).

Precise examples are given below.

1. Packaging by Capsule

Each capsule is for example formed of an envelope with a base of gelatine, glycerol, starch and colourants, the said envelope containing:

360 mg of nut oil;
  5 mg of althaea extract;
  6.5 mg of ginseng extract;
  75 mg of hop extract;
  20 mg of milk proteins rich in tryptophanes;
and, as vehicles and technological agents:
  yellow beeswax;
  soya lecithin at the rate of approximately 70 mg.

2. Packaging by Phial

Following the same logic, a phial contains by way of example:

720 mg of nut oil;
  10 mg of althaea extract;
  13 mg of ginseng extract;
  150 mg of hop extract;
  40 mg of milk proteins rich in tryptophanes;
and, as vehicles and technical agents:
  fruit juice;
  ovophospholipids; and
  antioxidant products.

3. Integration in a Chocolate

Lastly, an anti-stress chocolate can be made up in the following manner:

sugar;
  cocoa paste;
  cocoa butter;
  nut powder in a quantity corresponding to 720 mg of nut oil;
  10 mg of althaea extract;
  13 mg of ginseng extract;
  150 mg of hop extract;
  40 mg of milk proteins rich in tryptophanes;
and, as technological agents:
  soya lecithin; and
  flavourings.

In accordance with an alternative, the composition of the invention can even be incorporated in essential oils.

The invention will be better understood with reference to FIG. 1, which includes a diagram summarising on the one hand the effects of stress on the human organism and the need to respond to these effects with three types of action provided by the composition of the invention. In summary, stress can be caused during daily situations experienced by the patients, such as fear, pain, hypoglycaemia causing as mentioned above an increase in the levels of the stress hormones (in particular cortisol) in the blood. Where stress is prolonged, the behaviour of the patient is modified (flight, aggression, depression) and he experiences in particular memory and sleep problems. Lastly, a prolonged stress situation leads to a reduction of the immune defences, and consequently an increased susceptibility to infections.

To respond to the damaging effects of a stress situation and/or memory problems, the product of the invention applies a calming (C) and hormone stress regulating (R) action. To respond to sleep problems, the said composition applies a calming action (C). Lastly, the final immune stimulation action (I) permits correction of the reduction in the immune defences.

The present invention has been described by means of a composition example which is in no way limiting to the invention. On the contrary, this includes the modifications which are within the capability of the man skilled in the art.

What is claimed is:

1. An anti-stress composition intended to be incorporated in nutritional vehicles, assimilable by the human organism, to provide a calming, stress hormone regulating and immune stimulation effect, which comprises:
   a. at least one component including a combination of linoleic and linolenic acids in a proportion wherein the linoleic acid is about 58%, and the linolenic acid is about 13%, respectively; and
   b. at least one component taken from the flavonoid group.

2. The anti-stress composition according to claim 1, wherein the component including the combination of linolenic and linoleic acids is nut oil.

3. The anti-stress composition according to claim 1, wherein the flavonoid component is ginseng, in the form of ginsenosides and other saponines.

4. The anti-stress composition according to claim 1, and also including hop (Humulus lupulus) extracts.

5. The anti-stress composition according to claim 1, and also including tryptophane.

6. The anti-stress composition according to claim 5, wherein the tryptophane is present in the form of a milk protein.

7. The anti-stress composition according to claim 6, wherein the tryptophane represents about 3%, by weight, of said milk protein.

8. The anti-stress composition according to claim 1, further including althaea extract.

9. The anti-stress composition as described in claim 1, wherein a dose for daily usage in accordance with the following proportions by weight comprises:
   a. about 600 to 4000 mg of nut oil;
   b. extract of ginseng such that the quantity of ginsenosides is about 1 and 30 mg;
   c. about 100 to about 400 mg of hop extract;
   d. about 40 to about 1000 mg fraction of milk proteins.

10. The composition as described according to claim 9, wherein a daily dose for daily usage in accordance with the following proportions by weight comprises:
    a. about 720 mg nut oil;
    b. about 13 mg extract of ginseng such that the quantity of ginsenosides is equal to about 1.6 mg;
    c. about 150 mg hop extract;
    d. about 40 mg fraction of milk proteins.

11. The composition according to claim 9, wherein althaea extract is present in the amount of about 10 mg.

12. The composition according to claim 10, wherein althaea extract is present in an amount of about 10 mg.

13. The composition according to claim 1, wherein the composition is incorporated in a package selected from the group consisting of:
    a. capsules;
    b. phials;
    c. microspheres;
    d. confectionery products; and
    e. preparations for cold and hot drinks.

14. The composition according to claim 9, wherein the composition is incorporated in a package selected from the group consisting of:
    a. capsules;
    b. phials;
    c. microspheres;
    d. confectionery products; and
    e. preparations for cold and hot drinks.

15. The composition according to claim 10, wherein the composition is incorporated in a package selected from the group consisting of:
    a. capsules;
    b. phials;
    c. microspheres;
    d. confectionery products; and
    e. preparations for cold and hot drinks.

16. The composition according to claim 1, wherein it is incorporated in essential oils.

17. The composition according to claim 9, wherein it is incorporated in essential oils.

18. The composition according to claim 10, wherein it is incorporated in essential oils.

* * * * *